United States Patent [19]
Sato

[11] Patent Number: 5,728,734
[45] Date of Patent: Mar. 17, 1998

[54] PESTICIDE PREPARATION OF AQUEOUS SUSPENSION TYPE

[75] Inventor: Yoshihiro Sato, Chiba, Japan

[73] Assignee: Dainippon Ink and Chemicals, Inc., Tokyo, Japan

[21] Appl. No.: 603,123

[22] Filed: Feb. 20, 1996

[30] Foreign Application Priority Data

Feb. 23, 1995 [JP] Japan ................................. 7-35137

[51] Int. Cl.$^6$ ........................... A01N 37/52; A01N 33/04
[52] U.S. Cl. ...................... 514/555; 514/554; 514/634; 514/635; 514/937; 514/938; 514/970
[58] Field of Search ................................. 514/555, 554, 514/634, 635, 937, 938, 970

[56] References Cited

U.S. PATENT DOCUMENTS

| | | | |
|---|---|---|---|
| 4,659,739 | 4/1987 | Yoshioka et al. | 514/555 |
| 4,945,112 | 7/1990 | Zipplies et al. | 514/555 |

FOREIGN PATENT DOCUMENTS

| | | |
|---|---|---|
| 2-7564 | 2/1990 | Japan . |
| 2-188502 | 7/1990 | Japan . |
| 2-279607 | 11/1990 | Japan . |

*Primary Examiner*—John Pak
*Attorney, Agent, or Firm*—Armstrong, Westerman, Hattori, McLeland & Naughton

[57] ABSTRACT

A pesticide preparation of aqueous suspension type which comprises:
(a) a 1,1'-iminiodi(octamethylene)diguanidinium tris (alkyl-benzenesulfonate) as an active pesticide ingredient;
(b) at least one dispersion stabilizer selected from among alcohols having a degree of ethoxylation of 0 to 4 and carrying an alkyl group or an alkenyl group having 8 to 18 carbon atoms and phospholipids;
(c) at least one surfactant selected from among surfactants carrying an alkyl group or an alkenyl group having 6 to 20 carbon atoms; and
(d) water.

7 Claims, No Drawings

PESTICIDE PREPARATION OF AQUEOUS SUSPENSION TYPE

FIELD OF THE INVENTION

This invention relates to a stabilized pesticide preparation of aqueous suspension type which contains 1,1'-iminiodi (octamethylene)diguanidinium tris(alkylbenzenesulfonate) as an active pesticide ingredient.

BACKGROUND OF THE INVENTION 1,1'-Iminiodi(octamethylene)diguanidinium tris (alkylbenzenesulfonate), which is the active pesticide ingredient of the preparation according to the present invention (hereinafter referred to simply as "the active pesticide ingredient of the invention"), is disclosed in JP-B-2-7564 as an excellent pesticide proper for agricultural and horticultural use (the term "JP-B" as used herein means an "examined Japanese patent publication"). Among all, the active pesticide ingredients of the invention having $C_{10}$ to $C_{13}$ alkyl groups comprising $C_{12}$ alkyl group as the major component (m.p.: 92°–96° C.) have been named iminoctadine tris (albesilate) and already put into practical use as bactericides having broad spectra.

A pesticide proper, which is in the form of a solid at ordinary temperatures, may be processed into a preparation of aqueous suspension type generally by blending a water-soluble or water-suspendable synthetic polymer compound, an anionic surfactant, a nonionic surfactant, etc. therewith. When the pesticide proper has a melting point of from 30 to 100° C., however, there arises a problem that in the aqueous suspension thus obtained, the dispersion collapses with the development of crystals due to the melting or solidification of the solid proper, which has been dispersed, under severe conditions with a large difference in temperature. In the case of an emulsified aqueous suspension, on the other hand, there arises another problem that the emulsion is broken while crystals are precipitated due to intragranular crystallization.

To solve these problems, JP-A-2-188502 discloses a method for improving the storage stability of an aqueous suspension of water-insoluble biocide grains (m.p.: 15°–80° C.) which comprises blending a carboxylic acid ester, in addition to common surfactants, with the pesticide proper and allowing the carboxylic acid ester to bleed onto the surface of the pesticide proper to thereby achieve a surface-modifying effect (the term "JP-A" as used herein means an "unexamined published Japanese patent application").

Regarding the active pesticide ingredient of the invention, JP-A-2-279607 discloses a pesticide preparation of aqueous suspension type wherein a bisphenol ester derivative is employed in order to improve the storage stability via the effect of bleeding onto the surface of the active pesticide ingredient of the invention.

However, the method of JP-A-2-188502 with the use of a carboxylic acid ester is insufficient in the effect of preventing the crystallization of the active pesticide ingredient of the invention. Thus a pesticide preparation of aqueous suspension type with an excellent storage stability can be hardly obtained thereby. On the other hand, the method of JP-A-2-279607 with the use of a bisphenol ester derivative makes it possible to prepare a stable pesticide preparation of aqueous suspension type. However, it is feared in recent years that such a derivative is poisonous to the environment and the human body. Accordingly, it is not always preferable to use such a derivative as an aid of a pesticide preparation and there is a tendency to regulate the use of the same.

Accordingly, an object of the present invention is to provide a stable pesticide preparation of aqueous suspension type which exerts little effect on the environment or the human body and suffers from neither any separation, sedimentation nor crystal development of the active pesticide ingredient of the invention during storage.

SUMMARY OF THE INVENTION

The present inventors have conducted extensive studies in order to solve the above-mentioned problems. As a result, they have successfully found out that a pesticide preparation of aqueous suspension type, which sustains a stable suspension even in a storage test consisting of high temperature (50° C.) low temperature (–10° C.) cycles and suffers from no crystallization, can be obtained by blending the active pesticide ingredient of the invention with a specific dispersion stabilizer, a specific surfactant and water, thus completing the present invention.

Accordingly, the present invention relates to a pesticide preparation of aqueous suspension type which comprises:

(a) a 1,1'-iminiodi(octamethylene)diguanidinium tris (alkyl-benzenesulfonate) as an active pesticide ingredient;

(b) at least one dispersion stabilizer selected from among alcohols having a degree of ethoxylation of 0 to 4 and carrying an alkyl group or an alkenyl group having 8 to 18 carbon atoms and phospholipids;

(c) at least one surfactant selected from among surfactants carrying an alkyl group or an alkenyl group having 6 to 20 carbon atoms; and (d) water.

DETAILED DESCRIPTION OF THE INVENTION

The active pesticide ingredient (a) is a 1,1'-iminiodi (octamethylene)diguanidinium tris(alkylbenzenesulfonate) which is substantially insoluble in water. The alkyl chain of the alkylbenzenesulfonatic acid in this active pesticide ingredient is not particularly restricted. For example, those having 1 to 20 carbon atoms may be used therefor. There is no great difference in preparation in any case, so long as the alkyl chain is one falling within the scope as defined above. When pesticide-induced sufferings and pesticidal effects are taken into consideration, it is recommended to use an alkyl group having 4 to 18 carbon atoms. As the active pesticide ingredient of the invention, it is still preferable to use the compounds having $C_{10}$ to $C_{13}$ groups comprising $C_{12}$ alkyl group as the major component (hereinafter referred to as iminoctadine tris(albesilate)).

As the dispersion stabilizer (b) to be used in the present invention, use can be made of alcohols and/or phospholipids. The term "alcohols" as used herein means alcohols having a degree of ethoxylation of 0 to 4 and carrying an alkyl group or an alkenyl group having 8 to 18 carbon atoms.

The "degree of ethoxylation" is a value which stands for the number of ethoxy groups bonded to the hydroxyl group (s) in a molecule of an alcohol carrying an alkyl group having 8 to 18 carbon atoms (i.e., saturated aliphatic alcohol having 8 to 18 carbon atoms) or an alcohol carrying an alkenyl group having 8 to 18 carbon atoms (i.e., unsaturated aliphatic alcohol having 8 to 18 carbon atoms).

That is to say, an alcohol of a degree of ethoxylation of 1 means an alcohol wherein ethylene glycol is bonded to a saturated or unsaturated aliphatic alcohol via an ether bond. Such an alcohol is generally called a polyoxyethylene (1 mol) alkyl ether or a polyoxyethylene (1 mol) alkenyl ether.

An alcohol of a degree of ethoxylation of 3 means an alcohol wherein triethylene glycol is bonded to a saturated or unsaturated aliphatic alcohol via an ether bond. Such an alcohol is generally called a polyoxyethylene (3 mol) alkyl ether or a polyoxyethylene (3 mol) alkenyl ether. An alcohol of a degree of ethoxylation of 0 means a so-called saturated aliphatic alcohol (sometimes called an alkyl alcohol) wherein a hydroxyl group is bonded to the terminus of an alkyl group, or a so-called unsaturated aliphatic alcohol (sometimes called an alkenyl alcohol) wherein a hydroxyl group is bonded to the terminus of an alkenyl group.

Although the alkyl group or the alkenyl group may be either a linear or branched one so long as it has 8 to 18 carbon atoms, a linear one is preferable. It is preferable that the carbon atom number of the alkyl group or the alkenyl group is one almost the same as that of the alkyl group in the pesticide ingredient (a). It is still preferable that the carbon atom number is from 12 to 18.

Particular examples of the alcohols to be used in the present invention include linear alkyl alcohols such as octanol, decyl alcohol, lauryl alcohol, cetyl alcohol and stearyl alcohol; linear alkenyl alcohols such as oleyl alcohol; branched alkyl alcohols such as 2-ethyl-hexyl alcohol and 2-ethyl-hexyl diglycol; polyoxyethylene alkyl ethers having a degree of ethoxylation of 1 to 4 such as polyoxyethylene (1–4 mol) lauryl ethers and polyoxyethylene (1–4mol) cetyl ethers; and polyoxyethylene alkenyl ethers having a degree of ethoxylation of 1 to 4 such as polyoxyethylene (1–4mol) oleyl ethers. It is preferable to use an alcohol of a degree of ethoxylation of 0 therefor.

The term "phospholipids" to be used in the present invention is a general name involving lipids containing phosphorus and nitrogen which are usually produced from oil seeds such as soybean, yolk, etc. Particular examples of these phospholipids, which are called lecithin, include mixed phospholipids such as soybean lecithin, rapeseed lecithin, cotton seed lecithin, yolk lecithin, etc., phospholipids called lysolecithin which are obtained by treating the above-mentioned phospholipids with enzymes, and phospholipids obtained by the fractional purification of the above-mentioned mixed phospholipids such as phosphatidylcholine, phosphatidylethanolamine, etc. Among these phospholipids, soybean lecithin is particularly preferable.

As the dispersion stabilizer (b) to be used in the present invention, use can be made of one or more substances selected from among the alcohols and the phospholipids as described above. It may be appropriately selected depending on the pesticide ingredient (a) employed. When the alkyl group in the pesticide ingredient (a) has a relatively long chain, it is preferable to use an alcohol having an alkenyl group. When the above-mentioned alkyl group has a relatively short chain, on the other hand, it is preferable to use an alcohol having an alkyl group. In order to stabilize the dispersion under particularly severe temperature conditions (i.e., large changes in temperature), it is preferable to blend phospholipids, in particular, soybean lecithin. The content thereof in the dispersion stabilizer (b) preferably ranges from 30 to 70%, though the present invention is not restricted thereto.

The alcohols to be used in the present invention are in the form of a liquid or a solid at ordinary temperatures, while the phospholipids are in the form of a solid at ordinary temperatures. These dispersion stabilizers (b) have been widely employed in the fields of cosmetics, foods, etc. Thus it has been confirmed that they are highly safe to the environment and human body. Moreover, each acts as a dispersion stabilizer of an aqueous suspension preparation of the active pesticide ingredient of the invention. When microscopically observed, therefore, the pesticide preparation of aqueous suspension type thus obtained shows no development of crystals.

The surfactant (c) to be used in the present invention is not particularly restricted, so long as it is a surfactant carrying an alkyl group or an alkenyl group having 6 to 20 carbon atoms. That is, neither the ionic properties nor the presence of other substituents cause any problem. Although the alkyl group or the alkenyl group may be either a linear or branched one, a linear one is preferable. It is preferable that the carbon atom number of the alkyl group or the alkenyl group is one almost the same as that of the alkyl group in the pesticide ingredient (a). It is still preferable that the carbon atom number is from 10 to 18.

Particular examples of the surfactant (c) to be used in the present invention are as follows.

(1) Nonionic surfactant of polyalkylene oxide type: for example, polyoxyalkylene alkyl ethers such as polyoxyethylene (20mol) lauryl ether and polyoxyethylene (15 mol) cetyl ether; polyoxyalkylene alkenyl ethers such as polyoxyethylene (12 mol) oleyl ether; polyoxyalkylene alkylamino ethers such as polyoxyethylene (12 mol) laurylamino ether; and polyoxyalkylene alkenyl aryl ethers such as polyoxyethylene (10 mol) nonyl phenyl ether.

(2) Nonionic surfactant of fatty acid ester type: for example, polyglycerol fatty acid esters such as decaglycerol oleate and decaglycerol laurate; polyalkylene glycol fatty acid esters such as polyethylene glycol (average molecular weight: 600) oleate; polyoxyalkylene polypropylene glycol fatty acid esters such as polyoxyethylene polypropylene glycol block copolymer oleate; polyoxyalkylene sorbitol fatty acid esters such as polyoxyethylene (20 mol) sorbitan laurate; and sucrose fatty acid esters such as sucrose laurate.

(3) Anionic surfactant: for example, alkyl sulfates such as sodium lauryl sulfate; polyoxyalkylene alkyl sulfates such as polyoxyethylene (20 mol) lauryl ether sulfate ammonium salt; and polyoxyalkylene alkyl aryl sulfates such as polyoxyethylene (6 mol) nonyl phenyl ether sulfate sodium salt.

(4) Cationic surfactants: for example, alkylammonium salts such as cetyltrimethylammonium chloride; and polyoxyalkylene alkylammonium salts such as polyoxyethylene (10 mol) oleylmethylammonium chloride.

(5) Ampholytic surfactant: for example, alkylbetaines such as lauryldimethylammoniobetaine; and alkylamine oxides such as lauryldimethylamine oxide.

As the surfactant to be used in the present invention, one or more surfactants may be selected from among the above-mentioned ones. It may be appropriately selected depending on the pesticide ingredient (a) and the dispersion stabilizer (b) employed. Among these surfactants, those free from any aromatic group are preferable. Particularly preferable examples thereof include polyoxyalkylene alkyl ethers, polyoxyalkylene alkylamino ethers, polyglycerol fatty acid esters, alkyl sulfates and polyoxyalkylene alkylammonium salts. To stabilize the dispersion at a low temperature, it is particularly preferable to use polyglycerol fatty acid esters therefor.

In the present invention, a composition comprising the above-mentioned active pesticide ingredient (a), the dispersion stabilizer (b) and the surfactant (c) is suspended in water (d) to thereby give a pesticide preparation of aqueous suspension type.

The pesticide preparation of aqueous suspension type according to the present invention preferably comprises the ingredients each in the amount as defined below:

(a) active pesticide ingredient of the invention: from 1 to 45% by weight, still preferably from 5 to 40% by weight;

(b) dispersion stabilizer: from 0.5 to 30% by weight, still preferably from 2 to 20% by weight;

(c) surfactant: from 0.5 to 20% by weight, still preferably from 1 to 10% by weight; and (d) water: from 10 to 90% by weight, still preferably from 40 to 80% by weight.

The weight ratio of the dispersion stabilizer (b) to the active pesticide ingredient of the invention (a) is generally 1:0.1–15, preferably 1:0.5–10.

The weight ratio of the surfactant (c) to [the active pesticide ingredient of the invention (a) + the dispersion stabilizer (b)] is generally 1:1 –150, preferably 1:5 –60.

The pesticide preparation of aqueous suspension type of the present invention may further contain other arbitrary ingredients, so long as the effects of the present invention are not deteriorated thereby. For example, it may contain 0.2 to 20% of an antifreezing agent (a water-soluble organic solvent such as ethylene glycol, propylene glycol, propylene glycol monomethyl ether; and urea, etc.). It may furthermore contain other additives such as preservatives, pH regulating agents, defoaming agents, etc.

The pesticide preparation of aqueous suspension type of the present invention may be prepared by a publicly known method. For example, the active pesticide ingredient of the invention (a), the dispersion stabilizer (b) and the surfactant (c) are mixed together and, after adding water thereto, stirred in a homomixer, etc. Alternatively, the active pesticide ingredient of the invention (a) and the dispersion stabilizer (b) are mixed together and the obtained mixture is added to water in which the surfactant (c) has been dissolved. Then the resulting mixture is stirred in a homomixer, etc. to thereby give an aqueous suspension. It is also possible to further convert this aqueous suspension into fine grains with the use of a high-speed homogenizer or a high-pressure emulsifier.

To further illustrate the present invention in greater detail, and not by way of limitation, the following Examples will be given.

In the Examples and Comparative Examples of the present invention, each evaluation was performed by the following method under the conditions as specified below.

Storage stability (conditions):

(1) Stored at 50° C. for 12 weeks.

(2) Stored for 12 cycles each consisting of 3 days at 50° C. and 3 days at −10° C.

(3) Stored at −5° C. for 12 weeks.

Average grain size
  Measured with a coulter counter.

Viscosity
  Measured with a Brookfield type viscometer (30 rpm/20° C.).

Crystallization
  Observed under an optical microscope (400 × magnification).

EXAMPLE 1

30 parts by weight of iminoctadine tris(albesilate), the dispersion stabilizer (b) comprising 2 parts by weight of oleyl alcohol, 2 parts by weight of lauryl alcohol and 3 parts by weight of a phospholipid (Basis™ LP-20, soybean lecithin manufactured by The Nissin Oil Mills, Ltd.), the surfactant (c) comprising 3 parts by weight of decaglycerol oleate, and 5 parts by weight of ethylene glycol employed as an antifreezing agent were mixed together and heated to 50° C. to thereby give a homogeneous mixture. To the obtained mixture was slowly added water under stirring to thereby give 100 parts by weight of a suspension. This suspension was stirred in a homomixer at 10,000 rpm for 10 minutes. The preparation of aqueous suspension type thus obtained had the following properties.

Average grain size: 1.2 µm.

Viscosity: 180 mPa.s.

Storage stability: It sustained a good suspension under each of the conditions (1) to (3) as defined above.

Crystallization: No crystallization of the active pesticide ingredient was observed under each of the conditions (1) to (3) as defined above.

EXAMPLE 2

30 parts by weight of iminoctadine tris(albesilate), the dispersion stabilizer (b) comprising 2 parts by weight of oleyl alcohol, 2 parts by weight of lauryl alcohol and 3 parts by weight of a phospholipid (Basis™ LP-20, manufactured by The Nissin Oil Mills, Ltd.), the surfactant (c) comprising 3 parts by weight of polyoxyethylene (20 mol) lauryl ether, and 5 parts by weight of ethylene glycol employed as an antifreezing agent were mixed together and heated to 50° C. to thereby give a homogeneous mixture. To the obtained mixture was slowly added water under stirring to thereby give 100 parts by weight of a suspension. This suspension was stirred in a homomixer at 10,000 rpm for 10 minutes.

The obtained preparation of aqueous suspension type had the following properties.

Average grain size: 1.4 µm.

Viscosity: 190 mPa.s.

Storage stability: It sustained a good suspension under each of the conditions (1) to (3) as defined above.

Crystallization: No crystallization of the active pesticide ingredient was observed under each of the conditions (1) to (3) as defined above.

EXAMPLE 3

20 parts by weight of iminoctadine tris(albesilate), the dispersion stabilizer (b) comprising 2 parts by weight of oleyl alcohol, 2 parts by weight of lauryl alcohol and 3 parts by weight of a phospholipid (Basis™ LP-20, manufactured by The Nissin Oil Mills, Ltd.), the surfactant (c) comprising 2 parts by weight of sodium lauryl sulfate, and 5 parts by weight of ethylene glycol employed as an antifreezing agent were mixed together and heated to 50° C. to thereby give a homogeneous mixture. To the obtained mixture was slowly added water under stirring to thereby give 100 parts by weight of a suspension. This suspension was stirred in a homomixer at 10,000 rpm for 10 minutes.

The obtained preparation of aqueous suspension type had the following properties.

Average grain size: 1.8 µm.

Viscosity: 220 mPa.s.

Storage stability: It sustained a good suspension under the conditions (1) and (2) as defined above. Under the condition (3), its flowability was lost. When returned to room temperature (20° C), a stable suspension could be obtained again.

Crystallization: No crystallization of the active pesticide ingredient was observed under each of the conditions (1) to (3) as defined above.

EXAMPLE 4

20 parts by weight of iminoctadine tris(albesilate), the dispersion stabilizer (b) comprising 2 parts by weight of oleyl alcohol, 2 parts by weight of lauryl alcohol and 3 parts by weight of a phospholipid (Basis™ LP-20, manufactured by The Nissin Oil Mills, Ltd.), the surfactant (c) comprising 2 parts by weight of cetylmethylammonium chloride and 2 parts by weight of polyoxyethylene (15 mol) laurylamino ether, and 5 parts by weight of ethylene glycol employed as an antifreezing agent were mixed together and heated to 50° C. to thereby give a homogeneous mixture. To the obtained mixture was slowly added water under stirring to thereby give 100 parts by weight of a suspension. This suspension was stirred in a homomixer at 10,000 rpm for 10 minutes.

The obtained preparation of aqueous suspension type had the following properties.

Average grain size: 1.9 μm.

Viscosity: 210 mPa.s.

Storage stability: It sustained a good suspension under the conditions (1) and (2) as defined above. Under the condition (3), its flowability was lost. When returned to room temperature (20° C.), a stable suspension could be obtained again.

Crystallization: No crystallization of the active pesticide ingredient was observed under each of the conditions (1) to (3) as defined above.

EXAMPLE 5

30 parts by weight of iminoctadine tris(albesilate), the dispersion stabilizer (b) comprising 4 parts by weight of decyl alcohol and 3 parts by weight of a phospholipid (Basis™ LP-20, manufactured by The Nissin Oil Mills, Ltd.), the surfactant (c) comprising 3 parts by weight of decaglycerol oleate, and 5 parts by weight of ethylene glycol employed as an antifreezing agent were mixed together and heated to 50° C. to thereby give a homogeneous mixture. To the obtained mixture was slowly added water under stirring to thereby give 100 parts by weight of a suspension. This suspension was stirred in a homomixer at 10,000 rpm for 10 minutes.

The obtained preparation of aqueous suspension type had the following properties.

Average grain size: 1.5 μm.

Viscosity: 205 mPa.s.

Storage stability: It sustained a good suspension under each of the conditions (1) to (3) as defined above.

Crystallization: No crystallization of the active pesticide ingredient was observed under each of the conditions (1) to (3) as defined above.

EXAMPLE 6

20 parts by weight of iminoctadine tris(albesilate), the dispersion stabilizer (b) comprising 3 parts by weight of polyoxyethylene (3 mol) lauryl ether and 3 parts by weight of a phospholipid (Basis™ LP-20, manufactured by The Nissin Oil Mills, Ltd.), the surfactant (c) comprising 3 parts by weight of decaglycerol oleate, and 5 parts by weight of ethylene glycol employed as an antifreezing agent were mixed together and heated to 50° C. to thereby give a homogeneous mixture. To the obtained mixture was slowly added water under stirring to thereby give 100 parts by weight of a suspension. This suspension was stirred in a homomixer at 10,000 rpm for 10 minutes.

The obtained preparation of aqueous suspension type had the following properties.

Average grain size: 2.1 μm.

Viscosity: 380 mPa.s.

Storage stability: It sustained a good suspension under the conditions (1) and (2) as defined above. Under the condition (3), its was thickened and thus became creamy. When returned to room temperature (20° C.), the viscosity was lowered and a stable suspension could be obtained again.

Crystallization: No crystallization of the active pesticide ingredient was observed under each of the conditions (1) to (3) as defined above.

EXAMPLE 7

30 parts by weight of iminoctadine tris(albesilate), the dispersion stabilizer (b) comprising 2 parts by weight of oleyl alcohol, 3 parts by weight of lauryl alcohol and 2 parts by weight of a phospholipid (Basis™ LP-20, manufactured by The Nissin Oil Mills, Ltd.), the surfactant (c) comprising 3 parts by weight of decaglycerol oleate, and 5 parts by weight of ethylene glycol employed as an antifreezing agent were mixed together and heated to 50° C. to thereby give a homogeneous mixture. To the obtained mixture was slowly added water under stirring to thereby give 100 parts by weight of a suspension. This suspension was stirred in a homomixer at 10,000 rpm for 10 minutes.

The obtained preparation of aqueous suspension type had the following properties.

Average grain size: 2.2 μm.

Viscosity: 340 mPa.s.

Storage stability: It sustained a good suspension under the conditions (1) and (2) as defined above. Under the condition (3), its was thickened and thus became creamy. When returned to room temperature (20° C.), the viscosity was lowered and a stable suspension could be obtained again.

Crystallization: No crystallization of the active pesticide ingredient was observed under each of the conditions (1) to (3) as defined above.

EXAMPLE 8

30 parts by weight of iminoctadine tris(albesilate), the dispersion stabilizer (b) comprising 6 parts by weight of 2-ethylhexyl diglycol, the surfactant (c) comprising 3 parts by weight of decaglycerol oleate, and 5 parts by weight of ethylene glycol employed as an antifreezing agent were mixed together and heated to 50° C. to thereby give a homogeneous mixture. To the obtained mixture was slowly added water under stirring to thereby give 100 parts by weight of a suspension. This suspension was stirred in a homomixer at 10,000 rpm for 10 minutes.

The obtained preparation of aqueous suspension type had the following properties.

Average grain size: 1.6 μm.

Viscosity: 160 mPa.s.

Storage stability: It sustained a good suspension under each of the conditions (1) to (3) as defined above.

Crystallization: No crystallization of the active pesticide ingredient was observed under each of the conditions (1) to (3) as defined above.

EXAMPLE 9

20 parts by weight of iminoctadine tris(albesilate), the dispersion stabilizer (b) comprising 2 parts by weight of oleyl alcohol and 3 parts by weight of lauryl alcohol, the surfactant (c) comprising 3 parts by weight of decaglycerol oleate, and 5 parts by weight of ethylene glycol employed as an antifreezing agent were mixed together and heated to 50° C. to thereby give a homogeneous mixture. To the obtained mixture was slowly added water under stirring to thereby give 100 parts by weight of a suspension. This suspension was stirred in a homomixer at 10,000 rpm for 10 minutes.

The obtained preparation of aqueous suspension type had the following properties.

Average grain size: 1.9 μm.

Viscosity: 205 mPa.s.

Storage stability: It sustained a good suspension under each of the conditions (1) to (3) as defined above.

Crystallization: No crystallization of the active pesticide ingredient was observed under each of the conditions (1) to (3) as defined above.

EXAMPLE 10

20 parts by weight of iminoctadine tris(albesilate), the dispersion stabilizer (b) comprising 2 parts by weight of stearyl alcohol and 3 parts by weight of lauryl alcohol, the surfactant (c) comprising 3 parts by weight of decaglycerol oleate, and 5 parts by weight of ethylene glycol employed as an antifreezing agent were mixed together and heated to 50° C. to thereby give a homogeneous mixture. To the obtained mixture was slowly added water under stirring to thereby give 100 parts by weight of a suspension. This suspension was stirred in a homomixer at 10,000 rpm for 10 minutes.

The obtained preparation of aqueous suspension type had the following properties.

Average grain size: 2.0 μm.

Viscosity: 320 mPa.s.

Storage stability: It sustained a good suspension under the conditions (1) and (2) as defined above. Under the condition (3), its flowability was lost. When returned to room temperature (20° C.), a stable suspension could be obtained again.

Crystallization: No crystallization of the active pesticide ingredient was observed under each of the conditions (1) to (3) as defined above.

EXAMPLE 11

20 parts by weight of iminoctadine tris(albesilate), the dispersion stabilizer (b) comprising 5 parts by weight of a phospholipid (Basis™ LP-20, manufactured by The Nissin Oil Mills, Ltd.), the surfactant (c) comprising 3 parts by weight of decaglycerol oleate, and 5 parts by weight of ethylene glycol employed as an antifreezing agent were mixed together and heated to 50° C. to thereby give a homogeneous mixture. To the obtained mixture was slowly added water under stirring to thereby give 100 parts by weight of a suspension. This suspension was stirred in a homomixer at 10,000 rpm for 10 minutes.

The obtained preparation of aqueous suspension type had the following properties.

Average grain size: 2.1 μm.

Viscosity: 390 mPa.s.

Storage stability: It sustained a good suspension under the conditions (1) and (2) as defined above. Under the condition (3), its flowability was lost. When returned to room temperature (20° C.), a stable suspension could be obtained again.

Crystallization: No crystallization of the active pesticide ingredient was observed under each of the conditions (1) to (3) as defined above.

COMPARATIVE EXAMPLE 1

20 parts by weight of iminoctadine tris(albesilate), 10 parts by weight of xylene employed as a dispersion stabilizer, 3 parts by weight of decaglycerol oleate employed as a surfactant and 5 parts by weight of ethylene glycol employed as an antifreezing agent were mixed together and heated to 50° C. to thereby give a homogeneous mixture. To the obtained mixture was slowly added water under stirring to thereby give 100 parts by weight of a suspension. This suspension was stirred in a homomixer at 10,000 rpm for 10 minutes.

The obtained preparation of aqueous suspension type had the following properties.

Average grain size: 3.9 μm.

Viscosity: 200 mPa.s.

Storage stability: It underwent sedimentation and separation under each of the conditions (1) to (3) as defined above.

Crystallization: The crystallization of the active pesticide ingredient was observed under each of the conditions (1) to (3) as defined above.

COMPARATIVE EXAMPLE 2

20 parts by weight of iminoctadine tris(albesilate), 3 parts by weight of polyoxyethylene (10 mol) lauryl ether employed as a dispersion stabilizer, 3 parts by weight of decaglycerol oleate employed as a surfactant and 5 parts by weight of ethylene glycol employed as an antifreezing agent were mixed together and heated to 50° C. to thereby give a homogeneous mixture. To the obtained mixture was slowly added water under stirring to thereby give 100 parts by weight of a suspension. This suspension was stirred in a homomixer at 10,000 rpm for 10 minutes.

The obtained preparation of aqueous suspension type had the following properties.

Average grain size: 2.1 μm.

Viscosity: 305 mPa.s.

Storage stability: It underwent sedimentation and separation under each of the conditions (1) to (3) as defined above.

Crystallization: The crystallization of the active pesticide ingredient was observed under each of the conditions (1) to (3) as defined above.

COMPARATIVE EXAMPLE 3

20 parts by weight of iminoctadine tris(albesilate), 10 parts by weight of butyl laurate employed as a dispersion stabilizer, 2 parts by weight of the ammonium salt of an acrylic acid/methyl acrylate copolymer employed as a dispersant and 5 parts by weight of ethylene glycol employed as an antifreezing agent were mixed together and heated to 50 ° C. to thereby give a homogeneous mixture. To the obtained mixture was slowly added water under stirring to thereby give 100 parts by weight of a suspension. This suspension was stirred in a homomixer at 10,000 rpm for 10 minutes.

The obtained preparation of aqueous suspension type had the following properties.

Average grain size: 3.0 μm.

Viscosity: 315 mPa.s.

Storage stability: It underwent sedimentation and separation under each of the conditions (1) to (3) as defined above.

Crystallization: The crystallization of the active pesticide ingredient was observed under each of the conditions (1) to (3) as defined above.

COMPARATIVE EXAMPLE 4

30 parts by weight of iminoctadine tris(albesilate), a dispersion stabilizer comprising 2 parts by weight of oleyl alcohol, 2 parts by weight of lauryl alcohol and 3 parts by weight of a phospholipid (Basis™ LP-20, manufactured by The Nissin Oil Mills, Ltd.), 3 parts by weight of polyoxyethylene (24 mol) styryl phenyl ether employed as a surfactant, and 5 parts by weight of ethylene glycol employed as an antifreezing agent were mixed together and heated to 50° C. to thereby give a homogeneous mixture. To the obtained mixture was slowly added water under stirring to thereby give 100 parts by weight of a suspension. This suspension was stirred in a homomixer at 10,000 rpm for 10 minutes.

The obtained preparation of aqueous suspension type had the following properties.

Average grain size: 2.8 μm.

Viscosity: 350 mPa.s.

Storage stability: it underwent sedimentation and separation under each of the conditions (1) and (2). Under the condition (3), its flowability was lost. When returned to room temperature (20° C.), no stable suspension could be obtained any more.

Crystallization: The crystallization of the active pesticide ingredient was observed under each of the conditions (1) to (3) as defined above.

Because of having an excellent storage stability, the pesticide preparation of aqueous suspension type of the present invention suffers from neither any separation, sedimentation nor crystal development of the active pesticide ingredient, even though it is stored for a prolonged period of time. Moreover, it is highly safe to the environment and users.

While the invention has been described in detail and with reference to specific examples thereof, it will be apparent to one skilled in the art that various changes and modifications can be made therein without departing from the spirit and scope thereof.

What is claimed is:

1. An aqueous suspension pesticide preparation which comprises:

(a) a 1,1'-iminiodi(octamethylene)diguanidinium tris (alkyl-benzenesulfonate) as an active pesticide ingredient;

(b) at least one dispersion stabilizer selected from the group consisting of alcohols having a degree of ethoxylation of 0 to 4 and carrying an alkyl group or an alkenyl group having 8 to 18 carbon atoms and phospholipids;

(c) at least one surfactant selected from the group consisting of surfactants carrying an alkyl group or an alkenyl group having 6 to 20 carbon atoms; and (d) water.

2. A pesticide preparation as claimed in claim 1, wherein the alkyl group of said active pesticide ingredient (a) is an alkyl having 10 to 13 carbon atoms.

3. A pesticide preparation as claimed in claim 1, wherein the alcohol of said dispersion stabilizer (b) is an alcohol having a degree of ethoxylation of 0.

4. A pesticide preparation as claimed in claim 1, wherein said dispersion stabilizer (b) is one containing a phospholipid.

5. A pesticide preparation as claimed in claim 4, wherein said phospholipid is soybean lecithin.

6. A pesticide preparation as claimed in claim 1, wherein said surfactant (c) is one containing a polyglycerol fatty acid ester.

7. A pesticide preparation as claimed in any of claims 1 to 6 which comprises from 1 to 45% by weight of said active pesticide ingredient (a), from 0.5 to 30% by weight of said dispersion stabilizer (b), from 0.5 to 20% by weight of said surfactant (c), and from 10 to 90% by weight of water (d).

* * * * *